U.S. Patent Number: 5,225,514
Date of Patent: Jul. 6, 1993

United States Patent
Kimura et al.

[54] AZO CONTAINING POLYURETHANES FOR DRUG DELIVERY TO THE LARGE INTESTINES

[75] Inventors: Yoshiharu Kimura, Ohmihachiman; Soonih Kim; Akio Nishiura, both of Mishima, all of Japan

[73] Assignee: Ono Pharmaceutical Co., Ltd., Osaka, Japan

[21] Appl. No.: 812,824

[22] Filed: Dec. 24, 1991

Related U.S. Application Data

[63] Continuation of Ser. No. 494,462, Mar. 16, 1990, abandoned.

[30] Foreign Application Priority Data

Mar. 17, 1989 [JP] Japan .................. 1-65136

[51] Int. Cl.$^5$ ............................. C08G 18/30
[52] U.S. Cl. ........................ 528/76; 528/85; 514/772.3
[58] Field of Search ............ 528/76, 85; 514/772.3; 424/78

[56] References Cited

U.S. PATENT DOCUMENTS 3,909,497  9/1975  Hendry et al. ............... 528/503
4,235,988  11/1990 Fildes et al. ............... 528/79
4,663,308  5/1987  Saffran ..................... 514/3

FOREIGN PATENT DOCUMENTS 0016654  10/1980  European Pat. Off.
0109624  5/1984   European Pat. Off.

OTHER PUBLICATIONS

Abstract for Meeting of the Society of Polymer Science, Japan.

Primary Examiner—Morton Foelak
Assistant Examiner—Rachel Johnson
Attorney, Agent, or Firm—Stevens, Davis, Miller & Mosher

[57] ABSTRACT

A polyurethane (I) of 1000 to 100,000 in average molecular weight, comprising plural segments, which are each structural units of A-B, A-C and A-D of the formulae:

$$-\overset{O}{\underset{\|}{C}}NH-R^1-NH-\overset{O}{\underset{\|}{C}}\text{-aza-}, \quad \text{A-B}$$

$$-\overset{O}{\underset{\|}{C}}NH-R^1-NH-\overset{O}{\underset{\|}{C}}-Z-R^2-Z- \quad \text{A-C}$$

and $$-\overset{O}{\underset{\|}{C}}NH-R^1-NH\overset{O}{\underset{\|}{C}}-O-R^3-O-; \quad \text{A-D}$$

the proportion of the said segments of A-B, A-C and A-D, i.e. x:y:z is in the molar ratio 0.01 to 0.8:0 to 0.80:0 to 0.99, provided that the sum of x, y and z is 1.0; each segment being produced by combining with repeat units of A, B, C and D of the formulae:

$$-\overset{O}{\underset{\|}{C}}-NH-R^1-NH\overset{O}{\underset{\|}{C}}-, \quad \text{A}$$

-aza-, B $$Z-R^2-Z \text{ and} \quad \text{C}$$

$$-O-R^3-O-; \quad \text{D}$$

wherein $R^1$ is a skeleton of a diisocyanate and the three $R^1$'s in each of segments A-B, A-C and A-D can be the same or different; aza is a group of the formula:

$$-Y^1-\underset{R^4}{\bigcirc}-N=N-\underset{R^5}{\bigcirc}-Y^2- \text{ or} \quad (i)$$

$$-Y^1-\underset{R^4}{\bigcirc}-N=N-\bigcirc-N=N-\underset{R^5}{\bigcirc}-Y^2-; \quad (ii)$$

wherein $Y^1$ and $Y^2$ which can be the same or different, are oxygen, imino(—NH—) or a group of the formula:

\*$R^6$—O, \*$R^6$—NH, O—$R^6$—O, \*NHCO—$R^6$—NH or \*CONH—$R^6$—NH;

wherein $R^6$ is alkylene and an atom or the end of the group, marked by * is bonded to phenyl ring;

$R^4$ and $R^5$ each are, independently, hydrogen, halogen, nitro or phenyl;

$R^2$ is polyalkylene glycol residue;

Z is oxygen or imino and the two Z's are the same;

$R^3$ is alkylene or a group of the formula:

$$R^7-O-R^8, R^7-NH-R^8 \text{ or } R^7-\underset{\underset{R^9}{|}}{N}-R^8;$$

wherein
$R^7$ and $R^8$ which can be the same or different, are alkylene; and
$R^9$ is alkyl;

each segment of the polyurethane being contained in the aforementioned proportion of x, y and z, is combined by block-type, random-type or a combination thereof, is degraded specifically in the large intestine. Therefore, by using the polyurethane as pharmaceutical adjuvants, the medicament can be delivered specifically to the large intestine and at a high concentration with hardly any degradation and absorption in the small intestine, after oral administration.

10 Claims, 5 Drawing Sheets

AZO CONTAINING POLYURETHANES FOR DRUG DELIVERY TO THE LARGE INTESTINES

This is a continuation of application Ser. No. 07/494,462, filed: Mar. 16, 1990, now abandoned.

FIELD OF THE INVENTION

The present invention relates to novel polyurethanes which are degraded in the large intestine, processes for their preparation and pharmaceutical adjuvants containing them as a main component. More particularly, the invention relates to polyurethanes which are degraded by azo-reducing enzyme, produced by a large number of intestinal bacteria existing in the large intestine, processes for their preparation and pharmaceutical adjuvants for oral administration, containing the said polyurethanes as a main component.

BACKGROUND OF THE INVENTION

Generally speaking, it has turned out that a medicament orally administered is absorbed in the small intestine and hardly reaches the lower part of the small intestine and the large intestine (colon and rectum). Up until now, there was known a pharmaceutical composition which was soluble in the intestine, to transmit a medicament to the lower part of the small intestine and to the large intestine. In this composition, the coating thereof is dissolved according to the rise in pH thereby releasing the medicament in the composition. However, the pH in the digestive organs of a living body changes during the day, is influenced by food, and further is different between individuals. Accordingly, it has been found that such medicaments are unexpectedly absorbed in the upper part of the small intestine or the composition is excreted without disintegration.

Another idea for transmitting a medicament to the large intestine, utilizing a medicament which has been chemically modified, i.e. a prodrug, has been designed. However, it also has the defect that it is absorbed in the upper part of the small intestine. Further, the medicament is caused to be administered in large amounts in order to transmit it to the large intestine at a sufficiently high concentration with the attendant increase in side effects. Furthermore, in a prodrug, a modified group is metabolized and released, and thus it is considered that side effects accompanying the toxicity to occur. For example, salicylazosulfapyridine, which is a prodrug of 5-aminosalicyclic acid, is reported by Peppercorn M. A. et al (see J. Pharmacol. Exp. Ther. 181: 555–562, 1972). It is reported that the modified group, sulfapyridine, has toxicity (International Pharmacy Journal, 1(6), 223–226, 1987).

On the other hand, it has been found that peptides, such as insulin, vasopressin, etc., administered orally, are degraded and inactivated by digestive enzymes, such as peptidase, in the small intestine, etc. and its bioavailability is extremely low. Therefore, it is a reasonable consideration that the absorption from the large intestine in which digestive enzymes hardly exist, may be effective. However, no pharmaceutical composition for oral administration for such purpose has been developed until now.

Metabolism in the large intestine is almost exclusively conducted by intestinal bacteria, different from other digestive mechanisms. In order to obtain high molecular compounds for coating which can be degraded specifically in the large intestine, this structure should be effectively constituted by considering the action of the intestinal bacteria. For example, cellulose, which is known to be metabolized by *Eschericia coli*, has an essential factor for high molecular compounds degraded in the large intestine, and has been utilized in various ways. However, cellulose and its derivatives are difficult to control the rate of degradation.

Another chemical bond severed by the action of intestinal bacteria is an aromatic-azo bond. It is known that the bond is reduced to an amino group by azo-reducing enzyme released by intestinal bacteria, as follows:

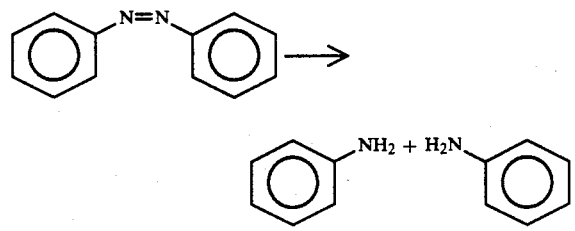

A coating polymer for delivering a medicament to the lower part of the digestive tract, by using the said enzymatic reaction, is proposed in the U.S. Pat. No. 4,663,308. It is a polymer derived from ethylenically unsaturated monomers (e.g. vinyl acetate, acrylic acid, methacrylic acid etc.) as the main chain, cross-linked by a divinylazobenzene of the formula:

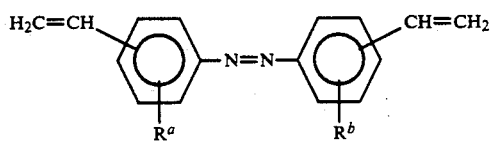

wherein $R^a$ and $R^b$ are each, independently, hydrogen, halogen, nitro or other substituents.

However, the cross-linked polymer is unstable to light and is difficult to be prepared at high conversion of the monomer to a polymer. Therefore, it has such defects that its solubility in various solvents is low and that its film-forming property is not good. Furthermore, it is difficult to precisely design the molecular structure so as to control the rate of release, and the like.

PURPOSE OF THE INVENTION

As a result of their energetic investigation in order to find high molecular compounds for coatings, having an excellent film-forming property and degrading specifically in the large intestine, the present inventors have found that their purpose is accomplished by using polyurethanes (I) having azo group(s) in the main chain.

The polyurethanes (I) of the present invention have azo group(s) in the main chain, and are not vinyl polymers but polyurethanes. At this point, the polymers of the present invention are remarkably different in structure from the polymers disclosed in the aforementioned U.S. Pat. No. 4,663,308 and are quite novel. Furthermore, the present polymers have excellent pharmaceutical properties, not suggested by the polymers in the aforementioned U.S. Patent.

SUMMARY OF THE INVENTION

The present invention relates to:

(1) polyurethanes (I) of 1000 to 100,000 in average molecular weight, comprising plural segments, which are each structural units of A-B, A-C and A-D of the formulae:

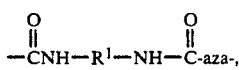   A-B

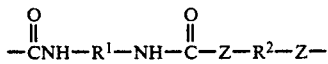   A-C and

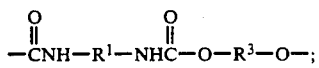   A-D the proportion of the said segments of A-B, A-C and A-D, i.e. x:y:z is in the molar ratio 0.01 to 0.8:0 to 0.80:0 to 0.99, provided that the sum of x, y and z is 1.0; each segment being produced by combining with repeat units of A, B, C and D of the formulae:

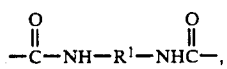   A

-aza-,   B $Z-R^2-Z$ and   C $-O-R^3-O-$;   D (2) processes for their preparation, and (3) pharmaceutical adjuvants containing the said polyurethanes (I) comprising plural segments as their main component.

In the formulae, $R^1$ is a skeleton of a diisocyanate and the three $R^1$'s is each of segments A-B, A-C and A-D can be the same or different; aza is a group of the formula:

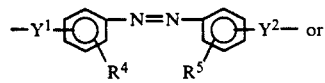   (i)

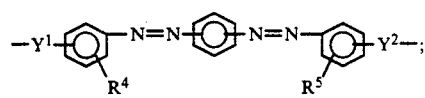   (ii)

wherein $Y^1$ and $Y^2$ which can be the same or different, are oxygen imino(—NH—) or a group of the formula:

*$R^6$—O, *$R^6$—NH,O—$R^6$—O, *NHCO—$R^6$—NH or *CONH—$R^6$—NH;

wherein $R^6$ is alkylene and an atom or the end of the group, marked by * is bonded to phenyl ring;

$R^4$ and $R^5$ each are, independently, hydrogen, halogen, nitro or phenyl;

$R^2$ is polyalkylene glycol residue;

Z is oxygen or imino and the two Z's are the same;

$R^3$ is alkylene or a group of the formula:

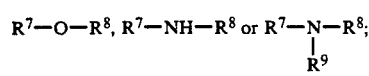

wherein $R^7$ and $R^8$ which can be the same or different, are alkylene; and $R^9$ is alkyl;

each segment of the polyurethane is contained in the aforementioned proportion of x, y and z, and is combined by block-type, random-type or a combination thereof.

DETAILED DESCRIPTION OF THE INVENTION

Figure 1:
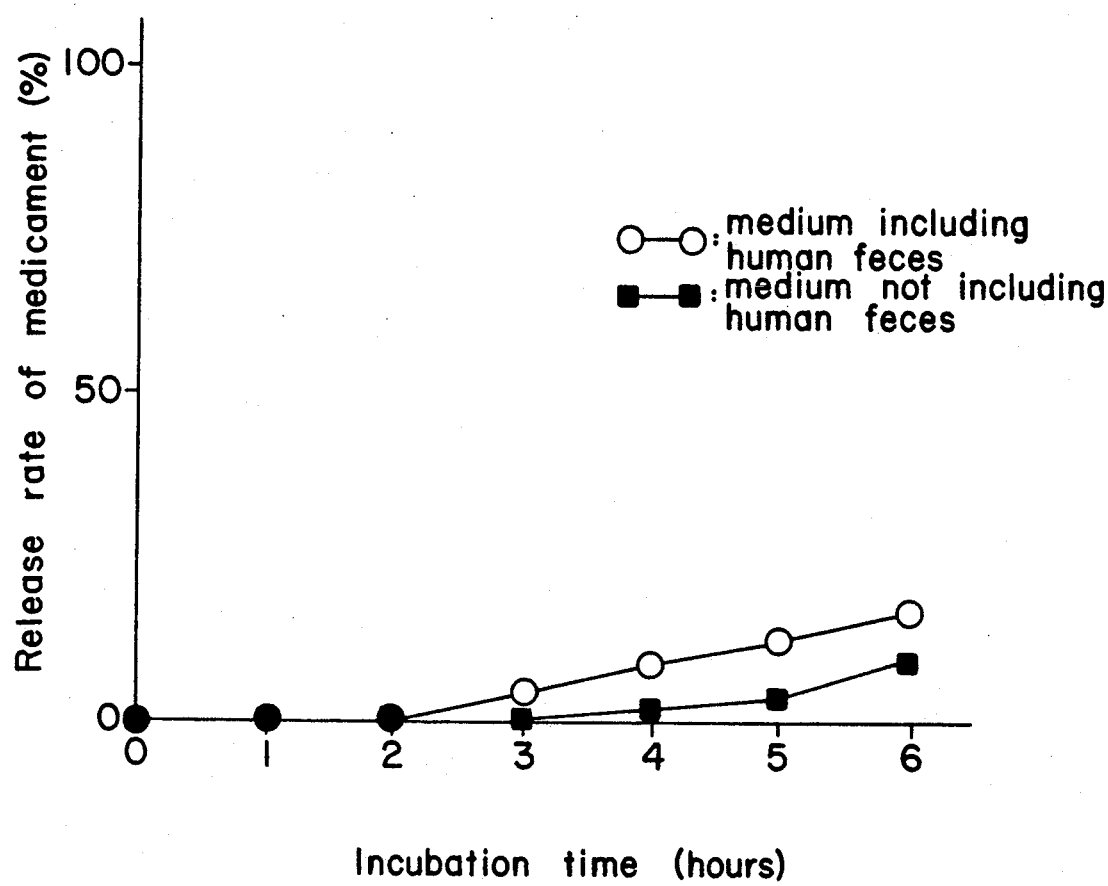
FIG. 1 is a graph showing the time-course of the release of a medicament in a composition coated with a polyurethane of the present invention, prepared in Example 13 (c).

In the present invention, unless otherwise specified, alkyl and alkylene include straight-chain and also branched-chain.

The bond to a benzene ring may be at any of the o-, m- and p-positions.

The segmented polyurethanes (I) of the present invention consist of four repeat units, A to D, and comprises an azo segment linking A to B, i.e. A-B, hydrophilic soft segment linking A to C, i.e. A-C and hydrophobic hard segment linking A to D, i.e. A-D. When the proportion of each segments is represented by x, y and z, respectively, x, y and z are any numerical value in the range of 0.01 to 0.8, 0 to 0.80 and 0 to 0.99, respectively, and the sum of x, y and z is 1.0. The total average molecular weight of the polyurethane of the invention are about 1000 to about 100,000.

Described in detail, the segment of A-B has an aromatic-azo group which is reduced by intestinal bacteria, and the polyurethanes are degraded by the chemical change of this segment. The segment of A-C is necesary for control of hydrophilicity of the polyurethanes. This segment increases the affinity of the polyurethane with the intestinal bacteria and further imparts water-solubility to a part of the polyurethane to increase the propensity of degrading a shaped product such as a coating. The segment of A-D is a hydrophobic hard segment, determining the physical property of the polyurethanes; controlling the solubility of the polyurethane in solvents and pharmacodynamics, and further greatly influencing the strength and characteristics of shaped products.

As $R^1$ in structural unit A, all divalent group known to those skilled in the art of high molecular compounds are included. Examples of such groups are aliphatic groups, such as $(CH_2)_4$, $(CH_2)_6$, $CH_2C(CH_3)_2CH_2CH_2CH(CH_3)CH_2$, $(CH_2)_8$, etc., aromatic groups such as $(CH_2)_8$, etc., aromatic groups such as

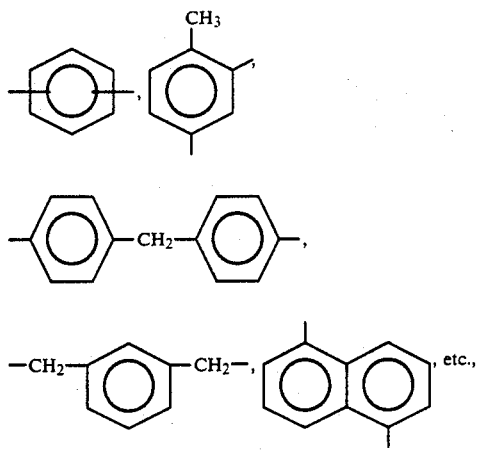

alicylic groups such as

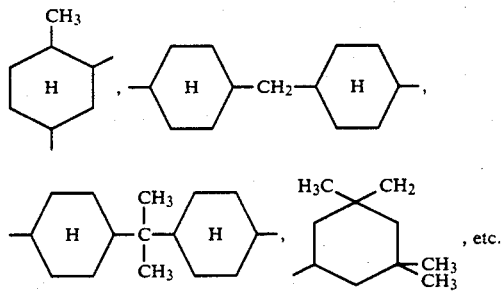

Examples of diisocyanates which give such groups are tetramethylene diisocyanate, hexamethylene diisocyanate, 2,2,5-trimethylhexamethylene diisocyanate, octamethylene diisocyanate, o-, m- or p-phenylene diisocyanate, 2,4- or 2,6-tolylene diisocyanate (abbreviated as TDI), 4,4'-diphenylmethane diisocyanate (abbreviated as MDI), o-, m- or p-xylylene diisocyanate, naphthalene 1,5-diisocyanate, hydrogenated TDI, hydrogenated MDI, dicyclohexyldimethylmethane 4,4'-diisocyanate, isophorone diisocyanate, etc. Further, such precursors of diisocyanates that produce an active diisocyanate, stabilized by a suitable blocking agent, may be used. Preferably $R^1$ is C4–8 alkylene, or a divalent group of a benzene or cyclohexyl, both of which may be unsubstituted or substituted by one to four methyl groups, and may be linked to the cyanate residues either directly or via one of the methyl groups. More preferably, $R^1$ is hexamethylene, xylylene or 3,5,5-trimethylcyclohexan-1-yl-3-ylmethyl.

As the azo-containing group, represented by the structural unit B, both the group having one azo group, shown by (i), and that having two azo groups, shown by (ii), are suitable to accomplish the present invention. $Y^1$ and $Y^2$ are the same or different, but preferably are the same. $Y^1$ and $Y^2$ may bond to phenyl rings at the same or different position. Examples of $Y^1$ and $Y^2$ are oxygen, imino, $*CH_2O$, $OCH_2CH_2O$, $*OCH_2CH_2NH$, etc. Examples of $R^4$ and $R^5$ are hydrogen, chlorine, nitro, phenyl, etc. Examples of azobenzene monomers having two functional groups, which give such group, are 4,4'-, 3,3'-, 3,4'-, 2,4'-, 2,2'-dihydroxyazobenzene, 1,4-bis[(4-hydroxyphenyl)azo]benzene, 4,4'-, 3,3'-, 2,2'-dihydroxymethylazobenzene, 4,4'-, 3,3'-, 2,2'-dihydroxyethylazobenzene, 4,4'-, 3,3'-, 2,2'-diaminoazobenzene, and derivatives thereof, e.g. diols, such as 4,4'-bis(2-hydroxyethoxy)azobenzene, diamines, such as 3,3'-bis-(aminoacetylamino)azobenzene, monoolamines, such as 3-(3-hydroxypropyloxy)-4'-(4-aminopropylcarbamyl-)azobenzene, etc.

Monomers in which are introduced a functional group at the o-position of an azo group are liable to be polymerized yielding polyurethanes having relatively low molecular weight.

Preferably $Y^1$ and $Y^2$ are oxygen, imino, or a group of the formula: $*R^6$-O or $*R^6$-NH (in which $R^6$ is C1–4 alkylene), more preferably oxygen, imino or $*CH_2O$.

Preferably, the aza group is:

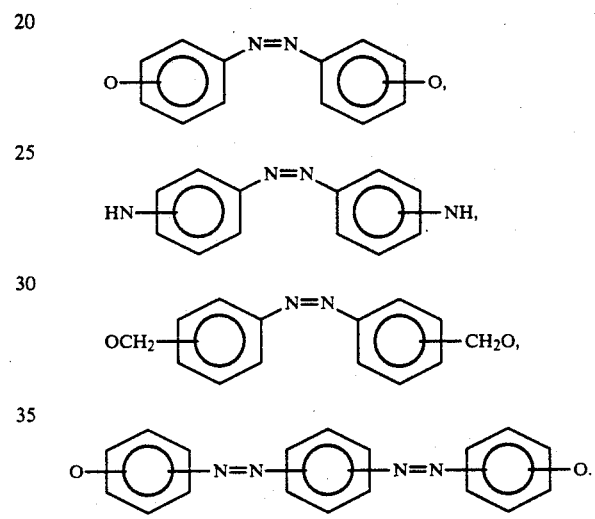

Examples of polyalkylene glycol residues represented by $R^2$ in structural unit C, are:

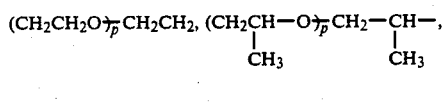

$(CH_2CH_2CH_2CH_2O)_p CH_2CH_2CH_2CH_2$;

in which p is the degree of polymerization and an integer from 1 to 500, preferably from 40 to 500, etc. The two Z's are the same, oxygen or imino, preferably oxygen.

Examples of polyalkylene glycols which give such groups are polyethylene glycol, polypropylene glycol, polytetramethylene glycol, poly(ethylenepropylene)-glycol (a copolymer of ethylene oxide and propylene oxide, having hydroxy groups at the both ends) all having an average molecular weight of about 70 to about 40000, preferably about 1000 to about 25000. Compounds having amino groups at the both ends, corresponding to the polyalkylene glycol, may be effectively used.

Preferably, the polyalkylene glycol is a polymer of C1–4 alkylene glycol, more preferably, polyethylene glycol.

Examples of $R^3$ in structural unit D are

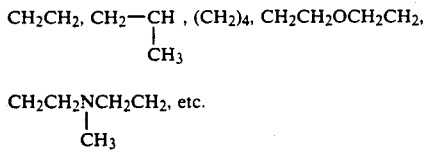

Examples of monomers which give such groups are aliphatic diols, such as ethylene glycol, 1,2-propylene glycol, trimethylene glycol, tetramethylene glycol, etc., diols having other functional groups, such as diethylene glycol, N-(2-hydroxyethyl)-N-methylethanolamine, etc., a diol having an aromatic group, etc. These diols may have other suitable substituents which do not react with the isocyanates. Preferably, $R^3$ is C1-6 alkylene or a group of the formula: $R^7$—O—$R^8$ (in which $R^7$ and $R^8$ are C1-6 alkylene), more preferably propylene, tetramethylene or 3-oxapentamethylene.

The polyurethanes (I) of the present invention can be prepared by methods known per se. That is, generally they may be formed by mixing an azobenzene monomer having two functional groups, which gives the structural unit B (merely referred to as azo compound (B) hereafter) with at least one of a polymer which gives the structural unit C (merely referred to as polymer (C) hereafter) and a diol compound which gives the structural unit D (merely referred to as diol compound (D) hereafter) in appropriate molar proportion, and then subjecting the mixture to polyaddition reaction with a diisocyanate which gives the structural unit A (merely referred to as diisocyanate (A) hereafter) in amounts equimolar with the sum of the three preceding compounds. It is clear that the proportion of segments A-B, A-C and A-D, of the obtained polyurethanes, i.e., x, y and z depends on the molar ratio of azo compound (B), polymer (C) and diol compound (D), used for the reaction. Usually the sequence of the segments is in irregular. Polyurethanes of the present invention having a block-type sequence of segments can be prepared by reacting azo compound (B) and an equimolecular proportion of diisocyanate (A), followed by at least one of (a) reacting polymer (C) and an equimolecular proportion of diisocyanate (A), and then reacting diol compound (D) and an equimolecular proportion of diisocyanate (A). Further, the polyurethane having a chain of short block-type sequence of segments can be prepared by subjecting the above to three polyadditions with mincing steps. Any of the polyurethanes above described can be degraded in the large intestine. Total molecular weight can be controlled by varying the sum of moles of the three kind of compounds reacting with diisocyanate (A).

The polyaddition reactions may be carried out in the presence of solvents or in bulk. The use of an appropriate catalyst can make the reaction proceed smoothly.

The characteristics and the degradation rate of the polyurethanes (I) are greatly changed by the proportion of each segment, x, y and z, which depend on the mole ratio of azo compound (B), polymer (C) and diol compound (D) as the starting materials. Generally speaking, the higher the proportion of the segment A-B or A-C is, the greater is the degradation rate by intestinal bacteria. The more preferable proportion of each segment, taking into account the degradation in the large intestine, the ease of treatment as coating agent and the release of a medicament is as follows:

(i) in the polymer of the present invention comprising segments of A-B and A-C, x:y is in the molar ratio less than 0.6 : more than 0.4, (ii) in that comprising segments of A-B and A-D, x:z is in the molar ratio less than 0.2: more than 0.8, and (iii) in that comprising segments of A-B, A-C and A-D, x:y:z is in the molar ratio less than 0.2: less than 0.1: more than 0.7, respectively.

The molecular weight of polyurethanes (I) can be changed according to the expected usage thereof. Preferably, the molecular weight of the polyurethane is about 8000 to 40000, relative to polystyrene standard, at the point of stability of the film. Polyurethanes having low molecular weight are suitable for use as the blending agents with other high molecular compounds which are applicable to medicament coating.

Furthermore, pharmaceutical adjuvants containing the polyurethane (I) as the main component are included in the present invention. The polyurethane (I) is degraded specifically in the large intestine, and therefore, it can be used as the pharmaceutical adjuvants for the purpose of delivering a medicament specifically to the large intestine at a high concentration. The term "adjuvant" as described herein means external coating agents for solid compositions for oral administration, such as tablets, granules, dispersible powders, pills and capsules, and carriers of sheet-like pharmaceutical composition in which a medicament is filled, etc.

Any medicament for the purpose of delivering specifically to the large intestine can be used without any restriction in the present invention. Examples of such medicaments include peptides, such as insulin, vasopressin, interferons, interleukins, etc.; guanidinobenzoic acid derivatives, such as gabexate mesylate, camostat mesylate, nafamostat mesylate, etc.; antiinflammatory agents such as aspirin, etc.; thromboxane $A_2$ antagonists such as 9α,11α-dimethylmethano-13-aza-14-oxo-15β-hydroxy-15-cyclopentyl-16,17,18,19,20-pentanor-11a-carbathromb-5Z-enoic acid, etc.

When the polyurethanes (I) of the present invention are used as external coating agents, they are dissolved or suspended into appropriate solvents (e.g. one or more of solvents selected from methylene chloride, chloroform, dioxane, acetone and ethanol) and then coated to a solid composition for oral administration separately prepared by a pan-coating method or a flow-coating method. If desired, water-insoluble polymers (e.g. ethyl cellulose, methacrylic acid copolymer, etc.) can be admixed in addition to the polyurethanes of the present invention.

When the polyurethanes (I) of the present invention are used as a sheet-like pharmaceutical composition, they are dissolved or suspended into appropriate solvents (as above mentioned) with a medicament, and are molded into films by using casting methods known per se. The films thus obtained are finely crushed and are filled into capsules, etc. If desired, in preparing the films, water-insoluble polymers (e.g. ethyl cellulose, methacrylic acid copolymer, etc.) and enteric polymer (e.g. hydroxypropylmethyl cellulose acetate succinate, carboxymethylethyl cellulose, etc.) can also be admixed.

EFFECT

By using the polyurethanes of the present invention as pharmaceutical adjuvants such that a medicament is filled into them or it is coated with them, the medicament can be delivered specifically to the large intestine and at a high concentration with hardly any degradation and absoption in the small intestine, after oral administration. Consequently, it is possible to design pharmaceutical compositions of reduced dose and side effects and improved bioavailability.

EXAMPLES

The following Examples, Reference Examples and Experimental Example illustrate but do not limit the present invention.

EXAMPLE 1

A solution of 0.5 g (0.0023 mol) of 2,2'-dihydroxyazobenzene (o-DHAB) and 1.7 g (0.0224 mol) of propylene glycol (PG) in 100 ml of N,N'-dimethylformamide (DMF) was heated at 150° C. with stirring under an atmosphere of nitrogen. When the reflux of DMF began, half of a solution of 5 g (0.030 mol) of hexamethylene diisocyanate (HMDI) in 50 ml of DMF was added dropwise all at once and vigorously stirred. The rest of the solution was added dropwise over three hours and the mixture thus obtained was refluxed for one hour. Then the reaction mixture was cooled to room temperature, and poured into 1000 ml of diethyl ether. The resulting precipitate was filtered and dried in vacuo to give 3.3 g of the following product. yield: 46%

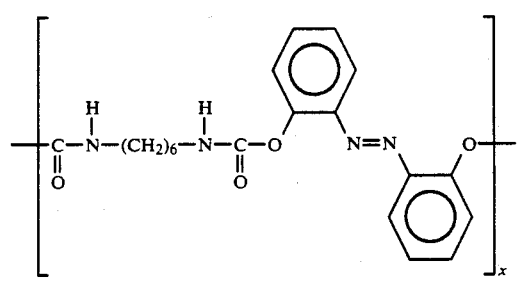

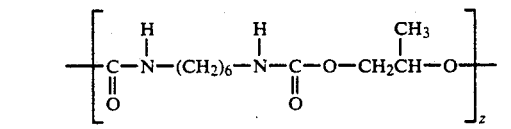

The product was confirmed to be polyurethane having the segments of formulae $I_{A-B}$ and $I_{A-D}$ by $^1$H-NMR spectroscopy measured with $D_7$-DMF as the solvent. The proportion of x:z was 0.09:0.91. The average molecular weight of the product was 1300 (relative to polystyrene standard, hereinafter shown as the value relative to polystyrene standard) by measuring a 1% tetrahydrofuran solution of the product by gel permeation chromatography (GPC).

EXAMPLE 2

A solution of 0.5 g (0.0023 mol) of o-DHAB and 1.7 g (0.224 mol) of PG in 20 ml of DMF was heated with stirring under an atmosphere of nitrogen. When the temperature of the mixture was at 100° C., half of a solution of 5 g (0.0265 mol) of m-xylylene diisocyanate (m-XDI) in 10 ml of DMF was added dropwise all at once and vigrously stirred. The rest of the solution was added dropwise over three hours and the mixture thus obtained was refluxed for one hour. Then the reaction mixture was cooled to room temperature, and poured into 200 ml of diethyl ether. The resulting precipitate was filtered and dried in vacuo to give 6.6 g of the following product. yield: 92%

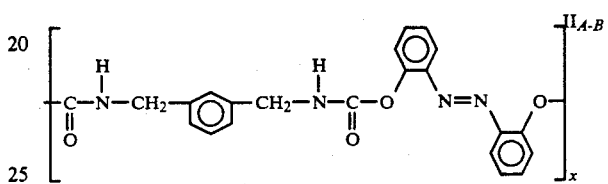

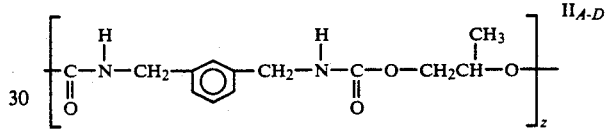

The product was confirmed to be polyurethane having the segments of formulae $II_{A-B}$ and $II_{A-D}$ by measuring in the same manner as example hereinbefore described. The proportion of x:z was 0.09:0.91. The average molecular weight of the product was 1700 by measuring in the same manner as example hereinbefore described.

EXAMPLE 3

A solution of 0.5 g (0.0024 mol) of 4,4'-diaminoazobenzene and 5 g (0.0025 mol) of polyethylene glycol (average molecular weight 2000, PEG-2000) in 20 ml of 1,4-dioxane was heated with stirring under an atmosphere of nitrogen. Refluxing at ca. 100° C., a solution of 0.87 g (0.0049 mol) of m-XDI in 5 ml of 1,4-dioxane was added thereto dropwise over three hours, and the mixture was further refluxed for one hour. Then, the reaction mixture was cooled to room temperature, and poured into 200 ml of diethyl ether. The resulting precipitate was filtered and dried in vacuo to give 5.1 g of the following product. yield: 80%

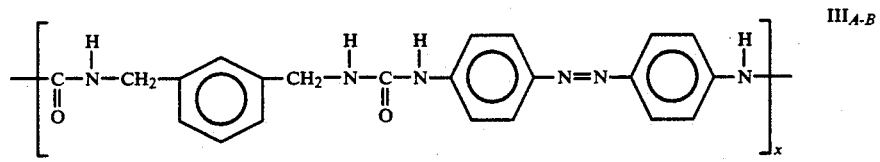

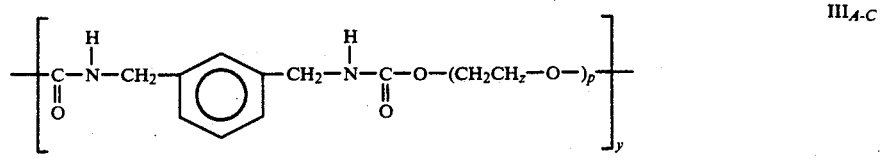

(wherein p is the degree of polymerization)

The product was confirmed to be polyurethane having the segments of formulae III$_{A-B}$ and III$_{A-C}$ by measuring in the same manner as examples hereinbefore described. The proportion of x:y=0.49:0.5. The average molecular weight of the product was 4800 by measuring in the same manner as examples hereinbefore described.

EXAMPLE 4

A solution of 2.5 g (0.0329 mol) of PG and 2.5 g (0.0013 mol) of PEG-2000 in 20 ml of 1,4-dioxane was heated with stirring under an atmosphere of nitrogen. Refluxing at ca. 100° C., a solution of 0.25 g (0.0012 mol) of 4,4'-diaminoazobenzene in 5 ml of 1,4-dioxane and 9.6 g (0.051 mol) of m-XDI were added thereto dropwise at the same time over three hours, and the mixture was further refluxed for one hour. Then, the reaction mixture was cooled to room temperature, and poured into 300 ml of diethyl ether. The resulting precipitate was filtered and dried in vacuo to give 10.6 g of the following product. yield: 71%

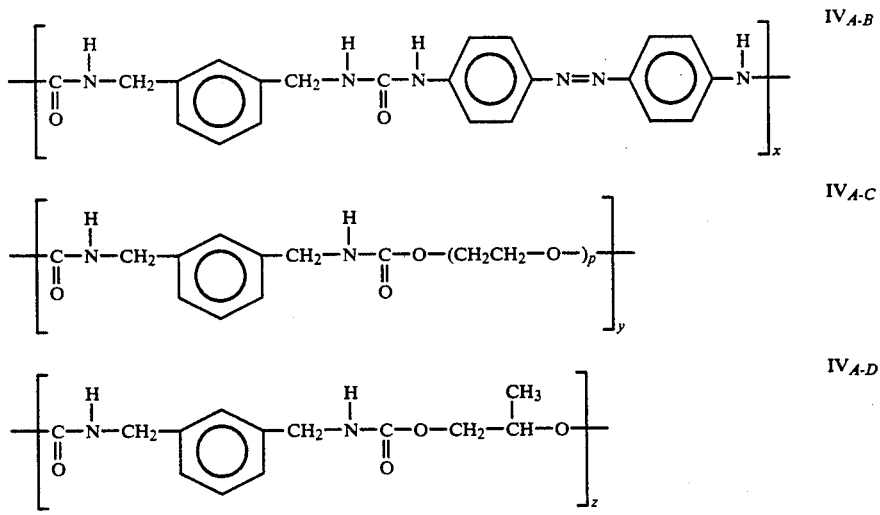

(wherein p is the degree of polymerization)

The product was confirmed to be polyurethane having the segments of formulae IV$_{A-B}$, IV$_{A-C}$ and IV$_{A-D}$ by measuring in the same manner as examples hereinbefore described. The proportion of x:y:z was 0.04:0.03:0.93. The average molecular weight of the product was 6400 by measuring in the same manner as examples hereinbefore described.

EXAMPLE 5

(a) A mixture of 1.05 g (0.0049 mol) of 3,3'-dihydroxyazobenzene (m-DHAB), 10 g (0.005 mol) of PEG-2000 and 10 g (0.131 mol) of PG was heated with stirring under an atmosphere of nitrogen. Half of 10 g (0.053 mol) of m-XDI was added dropwise all at once and vigorously stirred. The rest of m-XDI was added dropwise over three hours and further the mixture thus obtained was stirred for one hour at the same temperature to give a reddish brown transparent solid. The solid was dissolved in 100 ml of 1,4-dioxane, and the solution was poured into 1000 ml of n-hexane. The resulting precipitate was filtered and dried in vacuo to give 28.6 g of the following product. yield: 92%

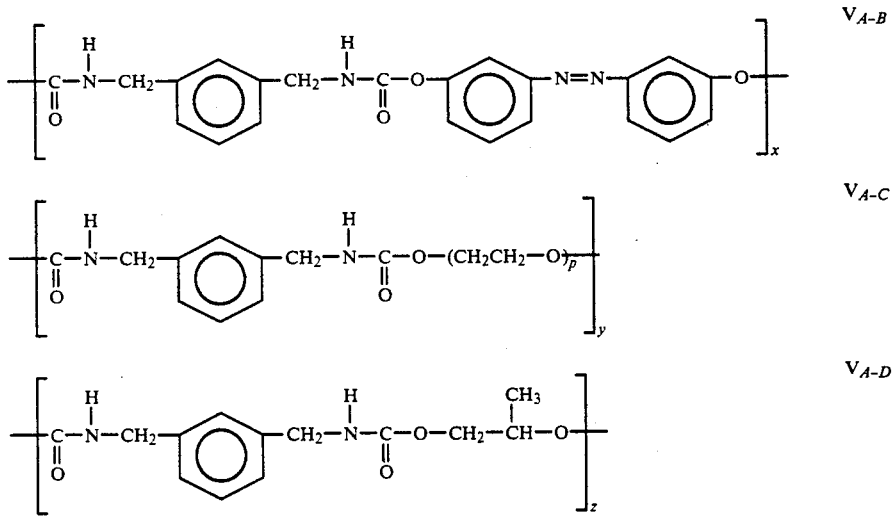

(wherein p is the degree of polymerization)

The product was confirmed to be polyurethane having the segments of formulae V$_{A-B}$, V$_{A-C}$ and V$_{A-D}$ by measuring in the same manner as examples hereinbefore described. The proportion of x:y:z was 0.035:0.035:0.930. The average molecular weight of the obtained was stirred for 30 minutes at the same temperature to give 33 g of reddish brown solid. yield: 90%

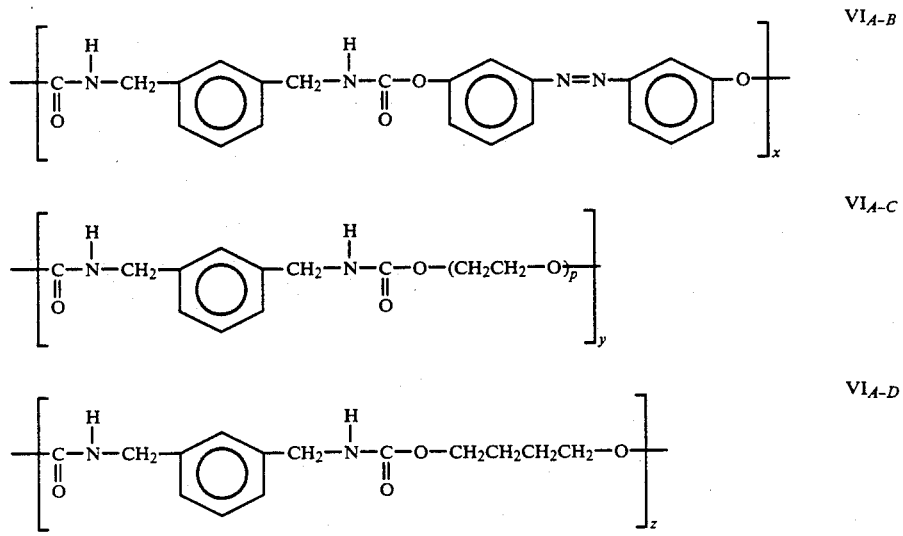

product was 18000 by measuring in the same manner as examples hereinbefore described.

(b) 31.3 g of polyurethane of the present invention was prepared by using 1.69 g (0.0079 mol) of m-DHAB, 11 g (0.0055 mol) of PEG-2000 and 11 g (0.144 mol) of PG. The proportion of x:y:z was 0.050:0.035:0.915. The average molecular weight of the product was 16100. yield: 93%

(c) 15.9 g of polyurethane of the present invention was prepared by using one g (0.0047 mol) of m-DHAB, 3.1 g (0.0016 mol) of PEG-2000 and 3.1 g (0.0407 mol) of PG. The proportion of x:y:z was 0.1:0.03: 0.87. The average molecular weight of the product was 18100. yield: 92%

EXAMPLE 6

A mixture of 1.6 g (0.0075 mol) of m-DHAB, 14 g (0.0007 mol) of polyethylene glycol (average molecular weight 20000, PEG-20000) and 6 g (0.0667 mol) of 1,4-butanediol was heated with stirring under an atmosphere of nitrogen. 15 g (0.0797 mol) of m-XDI was added dropwise over two hours and the mixture thus (wherein p is the degree of polymerization)

The product was confirmed to be polyurethane having the segments of formulae $VI_{A-B}$, $VI_{A-C}$ and $VI_{A-D}$ by measuring in the same manner as examples hereinbefore described. The proportion of x:y:z was 0.10:0.01:0.89. The average molecular weight of the product was 30000 by measuring in the same manner as examples hereinbefore described.

Further, the derivative of formula (VI) was prepared by using polyethylene glycol (average molecular weight 8300) as C component in the same manner.

EXAMPLE 7

A mixture of 0.945 g (0.0044 mol) of m-DHAB, 4 g (0.002 mol) of PEG-2000 and 4 g (0.0377 g) of diethylene glycol was heated with stirring under an atmosphere of nitrogen. 8.3 g (0.0441 mol) of m-XDI was added dropwise thereto over 30 minutes at 110° C. and the mixture was stirred for three hours at the same temperature to give reddish brown solid. The solid was dissolved in 100 ml of 1,4-dioxane, and the solution was poured into 1000 ml of n-hexane. The resulting precipitate was filtered and dried in vacuo to give 15.0 g of the product. yield: 87%

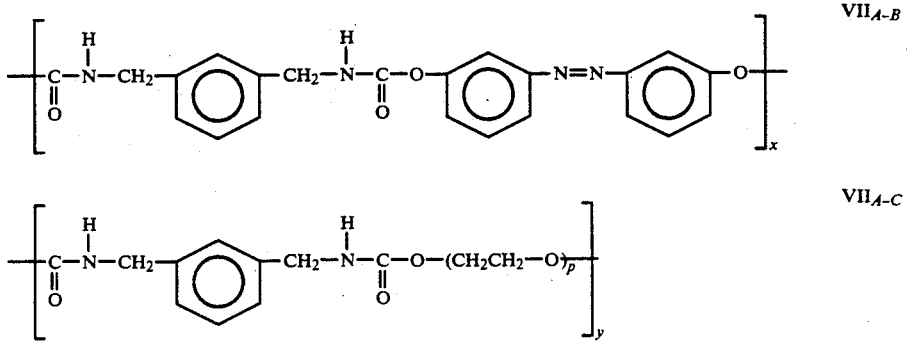

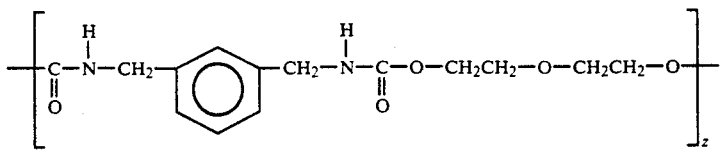

(wherein p is the degree of polymerization)

The product was confirmed to be polyurethane having the segments of formulae VII$_{A-B}$, VII$_{A-C}$ and VII$_{A-D}$ by measuring in the same manner as examples hereinbefore described. The proportion of x:y:z was 0.10:0.05:0.85. The average molecular weight of the product was 20000 by measuring in the same manner as examples hereinbefore described.

EXAMPLE 8

A mixture of 0.118 g (0.00055 mol) of m-DHAB, 0.5 g (0.00025 mol) of PEG-2000 and 0.5 g (0.00471 mol) of diethylene glycol was heated with stirring under an atmosphere of nitrogen. After raising the temperature to 65° C. to give a heterogeneous solution, 0.927 g (0.00551 mol) of HMDI was added. After raising the temperature of the mixture gradually with vigorously stirring, the mixture was stirred at 120° C. for 6 hours. The resulting solid was dissolved in 20 ml of 1,4-dioxane and the solution was poured into 200 ml of n-hexane. The resulting precipitate was filtered and dried in vacuo to give 1.98 g of the product. yield: 97%

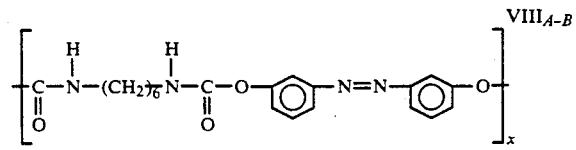

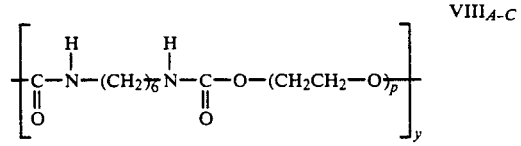

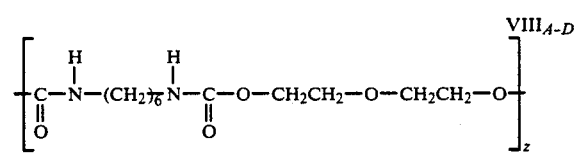

(wherein p is the degree of polymerization)

The product was confirmed to be polyurethane having the segments of formulae VIII$_{A-B}$, VIII$_{A-C}$ and VIII$_{A-D}$ by measuring in the same manner as examples hereinbefore described. The proportion of x:y:z was 0.1:0.045:0.855. The average molecular weight of the product was 20000 by measuring in the same manner as example hereinbefore described.

EXAMPLE 9

A mixture of 1.28 g (0.0060 mol) of m-DHAB, 4 g (0.002 mol) of PEG-2000 and 4 g (0.0526 mol) of PG was heated with stirring under an atmosphere of nitrogen. 10.26 g (0.061 mol) of HMDI was added dropwise thereto over three hours and the mixture was stirred for one hour at the same temperature to give a reddish brown transparent solid. The solid was dissolved in 200 ml of a mixture of ethanol and acetone (1:1), and the solution was poured into 2000 ml of n-hexane. The resulting precipitate was filtered and dried in vacuo to give 18.1 g of the product. yield: 98%

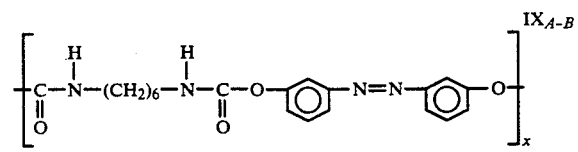

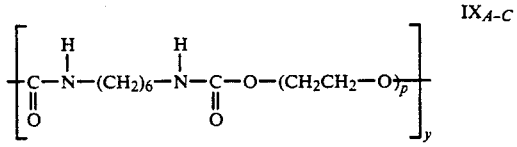

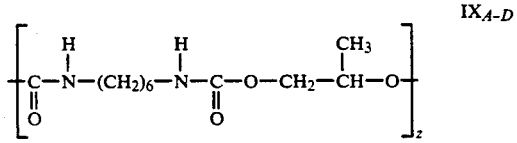

(wherein p is the degree of polymerization)

The product was confirmed to be polyurethane having the segments of formulae IX$_{A-B}$, IX$_{A-C}$ and IX$_{A-D}$ by measuring in the same manner as examples hereinbefore described. The proportion of x:y:z was 0.1:0.03:0.87. The average molecular weight of the product was 14000 by measuring in the same manner as examples hereinbefore described.

Several derivatives, having each segment of formula IX in various proportions were prepared in the same manner as above, by using various amounts of m-DHAB, PEG-2000 and PG as the starting materials. The average molecular weight of the products was in the range of 11000–14000. A polyurethane, wherein the proportion of x:y:z is 0.10:0.074:0.826, was obtained by using 1.029 g (0.0048 mol) of m-DHAB, 7 g (0.0035 mol) of PEG-2000 and 3 g (0.0394 mol) of PG as the starting materials. A polyurethane, wherein the proportion of x:y:z is 0.10:0.015:0.885, was obtained by using 1.114 g (0.0052 mol) of m-DHAB, 1.5 g (0.0008 mol) of PEG-2000 and 3.5 g (0.0460 mol) of PG as the starting materials.

EXAMPLE 10

A mixture of 3.63 g (0.015 mol) of 3,3'-dihydroxymethylazobenzene (m-DHMAB), 10 g (0.005 mol) of PEG-2000 and 10 g (0.132 mol) of PG was heated with stirring under an atmosphere of nitrogen. 25.4 g (0.151 mol) of HMDI was added dropwise thereto over three hours at 110° C. and the mixture was stirred for one hour at the same temperature to give a red transparent solid. The solid was dissolved in 300 ml of ethanol and the solution was poured into 3000 ml of n-hexane. The resulting precipitate was filtered and dried in vacuo to give 48.2 g of the product. yield: 98%

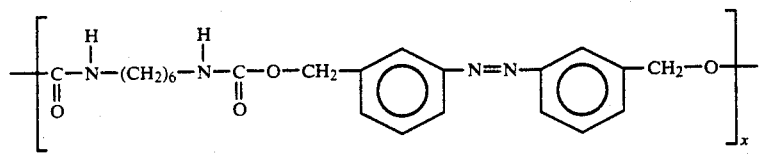

$X_{A-B}$

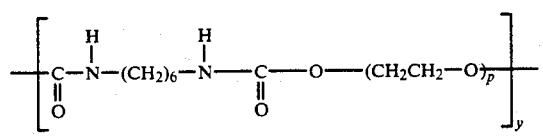

$X_{A-C}$

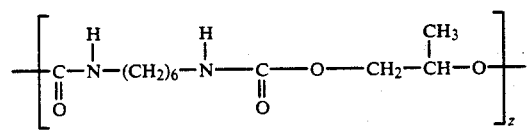

$X_{A-D}$ (wherein p is the degree of polymerization)

The product was confirmed to be polyurethane having the segments of formulae $X_{A-B}$, $X_{A-C}$ and $X_{A-D}$ by measuring in the same manner as examples hereinbefore described. The proportion of x:y:z was 0.10:0.03:0.87. The average molecular weight of the product was 43000 by measuring in the same manner as examples hereinbefore described.

In the same manner as above, a polyurethane wherein the proportion of x:y:z is 0.10:0.01:0.89 and an average molecular weight of 15000 was obtained by using 5.08 g (0.021 mol) of m-DHMAB, 6 g (0.003 mol) of PEG-2000 and 14 g (0.184 mol) of PG as the starting materials, and a polyurethane wherein the proportion of x:y:z is 0.10:0.07:0.83 and an average molecular weight of 16700, was obtained by using 2.32 g (0.0096 mol) of m-DHMAB, 14 g (0.007 mol) of PEG-2000 and 6 g (0.079 mol) of PG as the starting materials.

EXAMPLE 11

A solution of 0.73 g (0.0023 mol) of 1,4-bis[(4-hydroxyphenyl)azo]benzene and 1.7 g (0.0224 mol) of PG in 100 ml of DMF was heated to 150° C. with stirring under an atmosphere of nitrogen. When the reflux of DMF began, half of a solution of 5 g (0.030 mol) of HMDI in 50 ml of DMF was added dropwise all at once and the solution thus obtained was vigorously stirred. The rest of the solution of HMDI was added over three hours and the mixture was refluxed for one hour. Then the reaction mixture was cooled to room temperature, and poured into 1000 ml of diethyl ether. The resulting precipitate was filtered and dried in vacuo to give 3.5 g of the product. yield: 46%

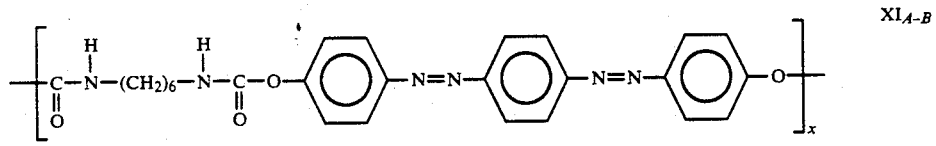

$XI_{A-B}$

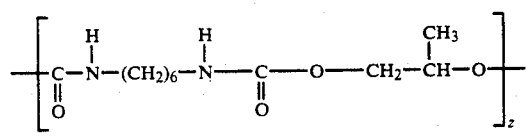

$XI_{A-D}$

The product was confirmed to be polyurethane having the segments of formulae $XI_{A-B}$ and $XI_{A-D}$ by measuring in the same manner as examples hereinbefore described. The proportion of x:z was 0.09:0.91. The average molecular weight of the product was 15000 by measuring in the same manner as examples hereinbefore described.

EXAMPLE 12

A mixture of 7.312 g (0.0302 mol) of m-DHMAB, 20 g (0.010 mol) of PEG-2000 and 20 g (0.262 mol) of PG was heated with stirring under an atmosphere of nitrogen. 67.132 g (0.302 mol) of isophorone diisocyanate was added dropwise thereto over three hours at 110° C. and the mixture was stirred for one hour at the same temperature to give a red transparent solid. The solid was dissolved in 300 ml of ethanol and the solution was poured into 3000 ml of diethyl ether. The resulting precipitate was filtered and dried in vacuo to give 87.131 g of the product. yield: 76%

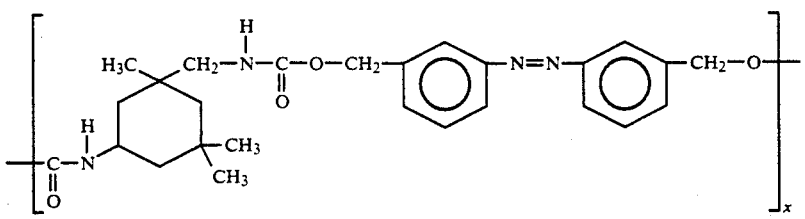 XII$_{A-B}$

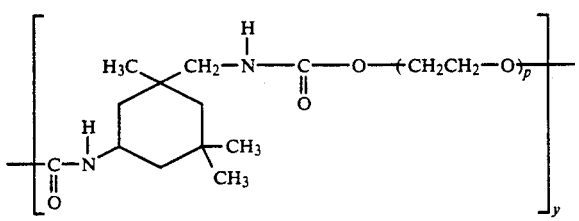 XII$_{A-C}$

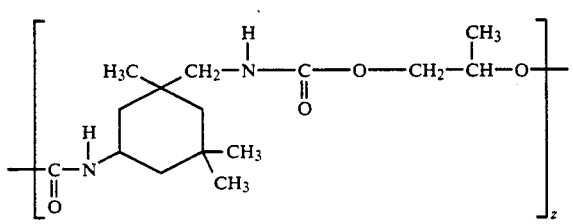 XII$_{A-D}$ (wherein p is the degree of polymerization)

The product was confirmed to be polyurethane having the segments of formulae XII$_{A-B}$, XII$_{A-C}$ and XII$_{A-D}$ by measuring in the same manner as examples hereinbefore described. The proportion of x:y:z was 0.10:0.03:0.87. The average molecular weight of the product was 10100 by measuring in the same manner as examples hereinbefore described.

REFERENCE EXAMPLE 1

5 parts in weight of p-(p-guanidinobenzoyloxy)-phenylacetic acid N,N-dimethylcarbamoylmethyl ester methanesulfonate, 3 parts in weight of lactose, 1 part in weight of microcrystalline cellulose (Avicel® PH 101, prepared by Asahi Kasei Co.) and 1 part in weight of low-substituted hydroxypropyl cellulose (L-HPC, prepared by Shinetsu Kagaku Co.) were admixed, and then granules of purified sugar (Nonparel® 103, Freund Ind. Ltd. Co.) as core were powder-coated with the mixture obtained by using a 5% aqueous solution of hydroxypropyl cellulose (HPC-L, prepared by Shinetsu Kagaku Co.) as binder, by centrifuged flow granulator (CF granulator, Freund Inc. Ltd. Co.) by the method known per se to obtain each pellets of about 1, 2 and 3 mm diameter.

EXAMPLE 13

The pellets prepared in Reference Example 1 were coated with a 5% solution of the polyurethane of the present invention, prepared in Example 1, in a mixture of acetone and ethanol (1:1) by a pan-coating method to obtain pharmaceutical compositions degraded in the large intestine, as in the present invention. Pharmaceutical compositions of the present invention were obtained in the same manner as above by using polyurethanes and solvents as shown in the following Table I.

TABLE I

| Example No. | used polyurethane | solvents |
|---|---|---|
| 13 (a) | Example 3 | chloroform/dioxane = 1/1 |
| 13 (b) | Example 5 (a) | chloroform/dioxane = 1/1 |
| 13 (c) | Example 5 (b) | chloroform/ethanol = 1/1 |
| 13 (d) | Example 5 (c) | methylene chloride/ethanol = 1/1 |
| 13 (e) | Exmaple 10 | acetone/ethanol = 1/1 |

REFERENCE EXAMPLE 2

One part in weight of 9α, 11α-dimethylmethano-13-aza-14-oxo-15β-hydroxy-15-cyclopentyl-16,17,18,19,20-pentanor-11a-carbathromb-5Z-enoic acid N-methyl-D-glucamine salt (abbreviated as Compound A hereafter), 5 parts in weight of lactose, 2 parts in weight of microcrystalline cellulose and 2 parts in weight of low-substituted hydroxypropyl cellulose were admixed, and then granules of purified sugar as core were powder-coated with the mixture obtained by using a 5% aqueous solution of hydroxypropyl cellulose as binder, by centrifuged flow granulator by the method known per se to obtain three kind of pellets of about 1, 2 and 3 mm diameter.

EXAMPLE 14 the pellets prepared in Reference Example 2 were coated with a 5% solution of the polyurethane of the present invention, prepared in Example 1, in a mixture of acetone and ethanol (1:1) by a pan-coating method to obtain pharmaceutical compositions degraded in the large intestine, as in the present invention. Pharmaceutical compositions of the present invention were obtained in the same manner as above by using polyurethanes and solvents as shown in the following Table II.

TABLE II

| Example No. | used polyurethane | solvents |
|---|---|---|
| 14 (a) | Example 3 | chloroform/dioxane = 1/1 |
| 14 (b) | Example 5 (a) | chloroform/dioxane = 1/1 |
| 14 (c) | Example 5 (b) | chloroform/ethanol = 1/1 |
| 14 (d) | Example 5 (c) | methylene chloride/ethanol = 1/1 |
| 14 (e) | Example 10 | acetone/ethanol = 1/1 |

REFERENCE EXAMPLE 3

250 g of Compound A, 740 g of glycerin tricaprylate (Panacete®800, prepared by Nippon Yushi Co.) and 10 g of bean lecithin (prepared by Hohnen Seiyu Co.) were admixed enough with stirring. The obtained suspension was sieved through a 100-mesh sieve and then was filled into soft capsules with a rotary-capsule machine by methods known per se to obtain about 2000 soft capsules.

EXAMPLE 15

The soft capsules prepared in Reference Example 3 were coated with a 5% solution of the polyurethane of the present invention, prepared in Example 1, in a mixture of acetone and ethanol (2:8) by a pan-coating method to obtain pharmaceutical compositions degraded in the large intestine, as in the present invention. Pharmaceutical compositions of the present invention were obtained in the same manner as above by using polyurethanes and solvents as shown in the following Table III

TABLE III

| Example No. | used polyurethane | solvents |
|---|---|---|
| 15 (a) | Example 3 | chloroform/dioxane = 1/1 |
| 15 (b) | Example 5 (a) | chloroform/dioxane = 1/1 |
| 15 (c) | Example 5 (b) | chloroform/ethanol = 1/1 |
| 15 (d) | Example 5 (c) | methylene chloride/ethanol = 1/1 |
| 15 (e) | example 10 | acetone/ethanol = 1/1 |

REFERENCE EXAMPLE 4

Three kind of pellets of about 1, 2 and 3 mm diameter were obtained by using 5 parts in weight of barium sulfate, 4 parts in weight of lactose, 1 part in weight of microcrystalline cellulose and 4 parts in weight of low-substituted hydroxypropyl cellulose, in the same manner as Reference Example 1.

EXAMPLE 16

The pellets prepared in Reference Example 4 were coated with a 5% solution of the polyurethane of the present invention, prepared in Example 1, in a mixture of ethanol and acetone (8:2) by a pan-coating method to obtain pharmaceutical compositions degraded in the large intestine, as in the present invention. Pharmaceutical compositions of the present invention were obtained in the same manner as above by using polyurethanes and solvents as shown in the following Table IV.

TABLE IV

| Example No. | used polyurethane | solvents |
|---|---|---|
| 16 (a) | Example 3 | chloroform/dioxane = 1/1 |
| 16 (b) | Example 5 (a) | chloroform/dioxane = 1/1 |
| 16 (c) | Example 5 (b) | chloroform/ethanol = 1/1 |
| 16 (d) | Example 5 (c) | methylene chloride/ethanol 1/1 |

TABLE IV-continued

| Example No. | used polyurethane | solvents |
|---|---|---|
| 16 (e) | Example 10 | acetone/ethanol = 1/1 |

EXPERIMENTAL EXAMPLE 1

Degradation of the polyurethane of the present invention

Method

Experiment was carried out by applying human feces-incubation method as described by T. Mitsuoka et. al., (Kansensho-Gakkai Zasshi, 45(9), 406–419, 1981).

That is, the semi-solid general anaerobic medium (GAM, Nissui Ltd. Co.) was added to approximately one gram of human feces to obtain the mixture of 10 g in weight. The mixture further diluted with GAM to 10 times to obtain the $10^{-2}$ fold medium. The medium thus obtained was incubated in approximately 200 fold GAM at 37° C. for two days anaerobically to obtain the test medium.

After the polyurethane films of the present invention were incubated in 20 ml of the test medium for two days, the degree of degradation of the films by the action of intestinal flora was investigated by measuring tensile strength, tensile elongation and molecular weight. Similarly, the experiment was carried out in the test medium not including human feces as control. The result was shown in the following Table V.

TABLE V

| Example No. of polyurethane | kind of test medium | average molecular weight | tensile strength (MPa) | tensile elongation (%) |
|---|---|---|---|---|
| 3 | (A) | 4800 | <30 | 250 |
|   | (B) | 4700 | <2 | 3 |
| 5(b) | (A) | 16100 | <122 | 540 |
|   | (B) | 17600 | <31 | 17 |
| 5(c) | (A) | 18100 | 1) | 1) |
|   | (B) | 9600 | 2) | 2) |
| 11 | (A) | 15000 | <55 | 450 |
|   | (B) | 13000 | <7 | 12 |

(A) means test medium not including human feces.
(B) means test medium including human feces.
1) It was impossible to measure because the films absorbed water to swell. It was confirmed by electron microscope that the surface of the film was smooth and the film was not degraded.
2) It was impossible to measure because of severe degradation of the film.

Consideration

It is understood that the tensile strength and elongation, of the polyurethane films of the present invention are remarkably reduced by the incubation thereof in a test medium including human feces, compared with the incubation in a test medium not including human feces. Further, the molecular weight of the polyurethane in a test medium including human feces tends to lower.

It is considered from the fact, that azo bonds in the polyurethane were involved in the chemical change by the action of intestinal bacteria living in human feces and thereby the structure of the film was changed and the tensile strength and tensile elongation thereof are reduced.

EXPERIMENTAL EXAMPLE 2

Release of a Medicament in Composition Coated with Polyurethane of the Present Invention

Method

The compositions prepared in Example 13(c), 13(d) and 14(d) were incubated in mediums including or not including human feces, used in Experimental Example 1. The medium was withdrawn after given periods of time and the medicament released in the medium was measured by high-performance liquid chromatography.

Result

Figure 2:
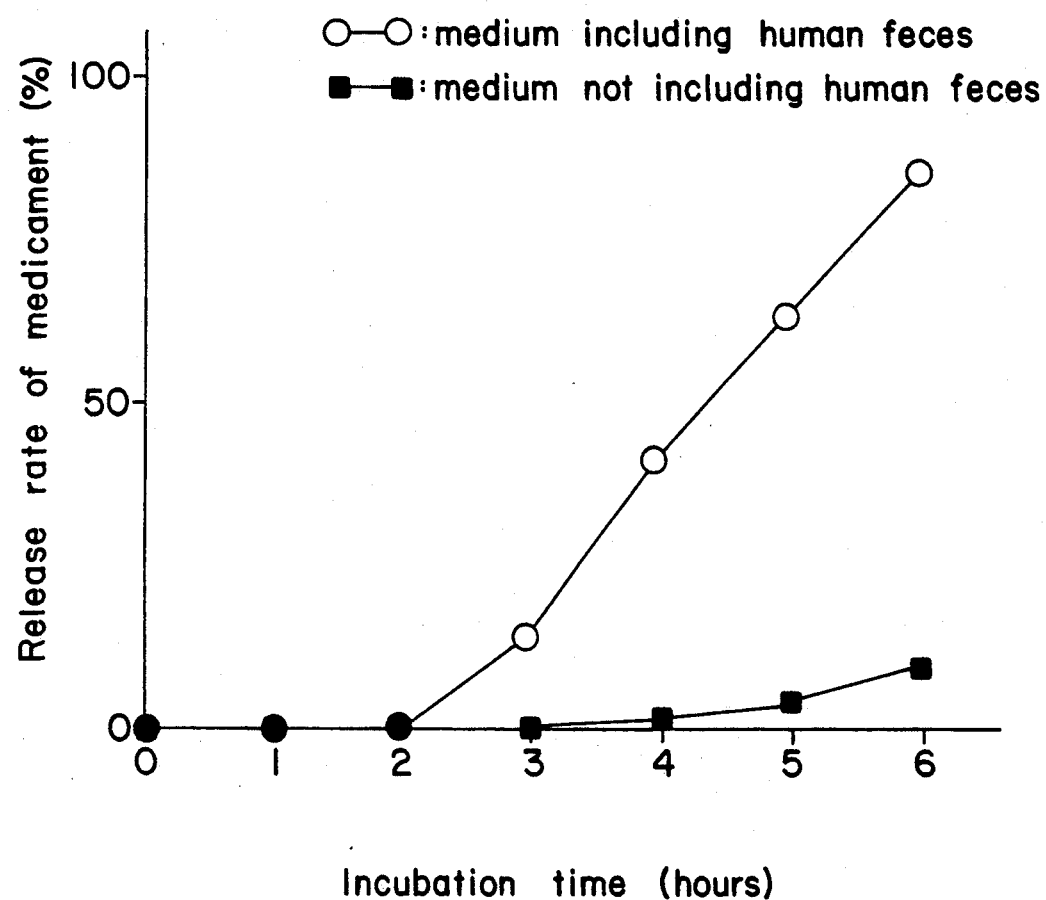
FIG. 2 is a graph showing the time-course of the release of a medicament in a composition coated with a polyurethane of the present invention, prepared in Example 13 (d).
Figure 3:
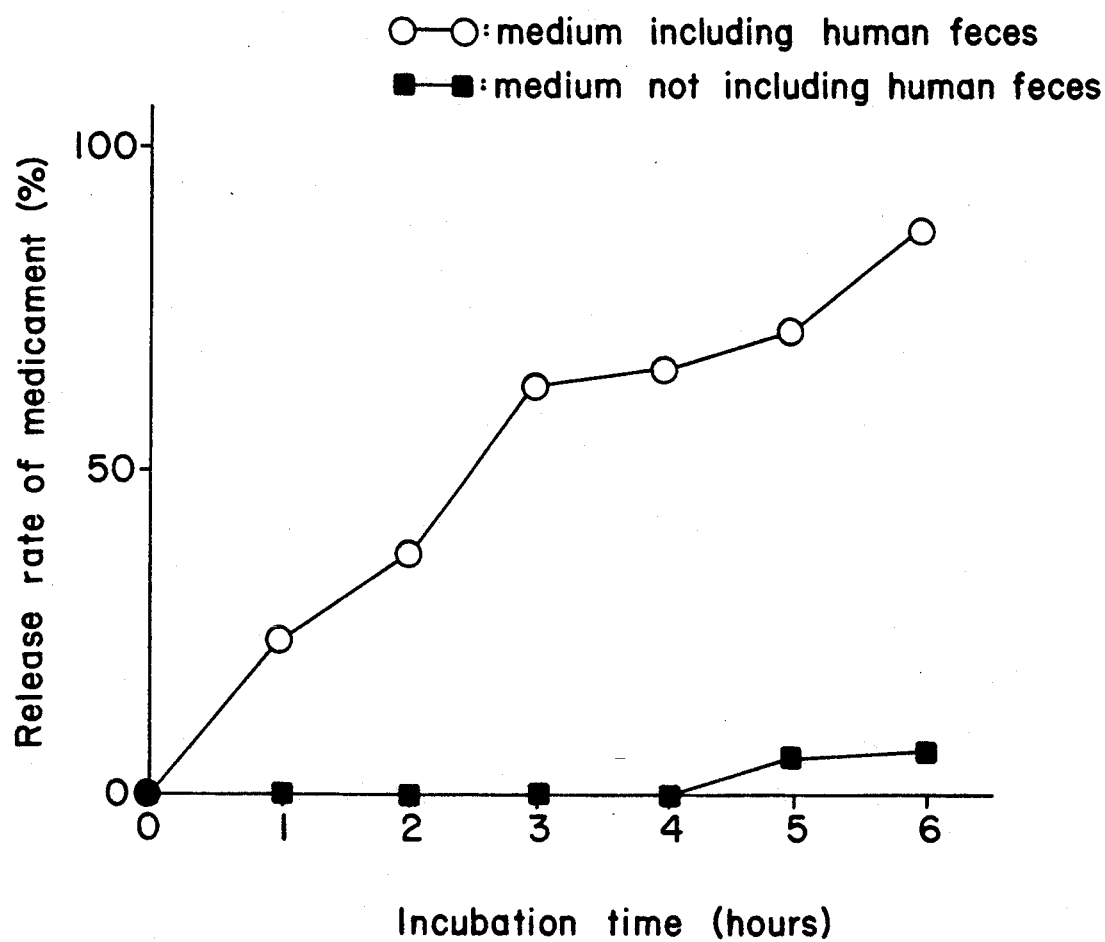
FIG. 3 is a graph showing the time-course of the release of a medicament in a composition coated with a polyurethane of the present invention, prepared in Example 14 (d).

Result was shown in FIGS. 1, 2 and 3.

Consideration

The release rate of a medicament in the composition of the present invention incubated in a medium including human feces was highly superior to that incubated in a medium not including human feces.

Furthermore, it is considered that the compositions having various release rate of a medicament are obtained according to the proportion x of segment containing aromatic azo groups.

EXPERIMENTAL EXAMPLE 3

Disintegration of a Medicament in Composition Coated with Polyurethane of the Present Invention in Oral Administration

Method

Compositions prepared in Example 16(d) (each 25 pellets) were administered orally with 50 ml of water in 14 beagle dogs fasting overnight. After given periods of time (2 dogs after 2 hours, 2 dogs after 3 hours, 6 dogs after 4 hours and 4 dogs after 5 hours), the dogs were anesthetized intravenously by sodium pentobarbital, and then photographed by X rays to trace the compositions in the digestive tract.

Result

Figure 4:
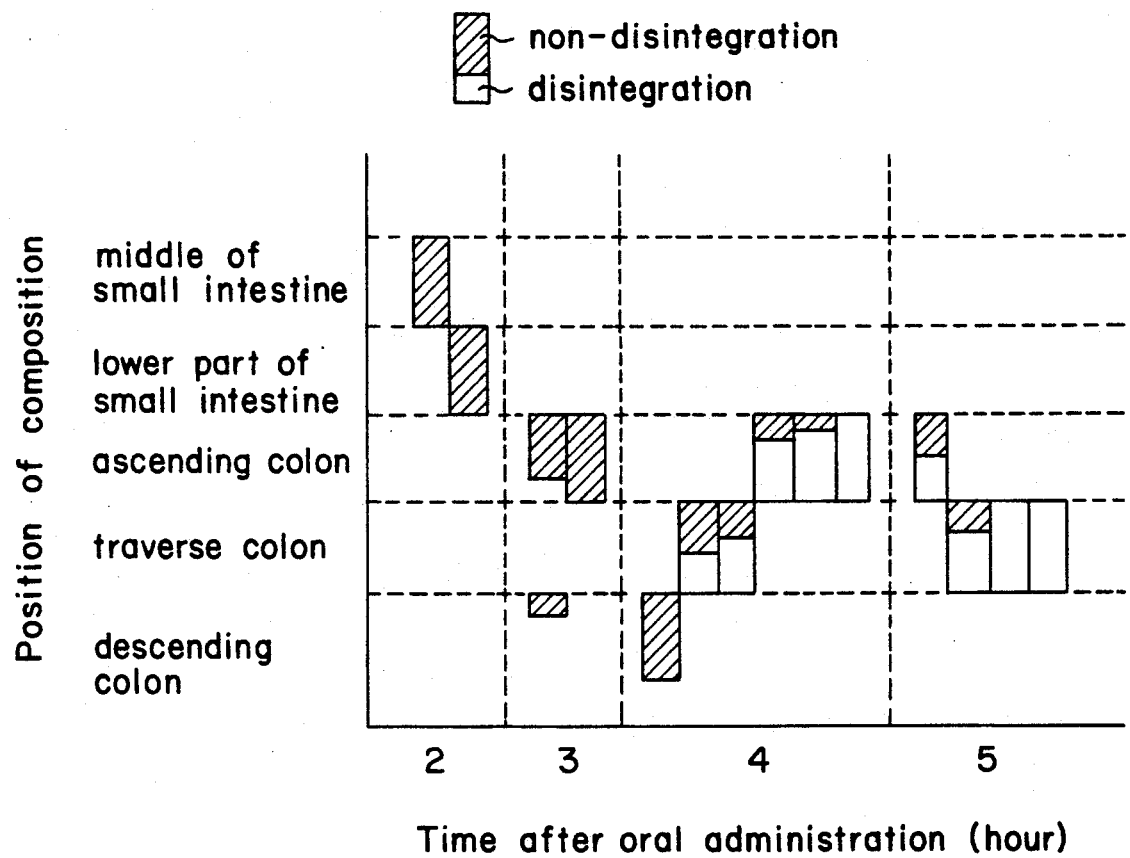
FIG. 4 is a figure showing the time-course of the position in the digestive tract and disintegration of a composition coated with a polyurethane of the present invention, prepared in Example 16 (d) in oral administration.

The result is shown in FIG. 4. In this figure, each oblong represents the total volume of pellets administered and represents the position of pellets after given periods of times. Opened and shaded parts in the oblong indicates the proportion of disintegration.

Consideration

It is confirmed that the compositions coated with polyurethane of the present invention reached the colon 3 hours after administration, and most of them were disintegrated in ascending and traverse colon after 4 hours, to release a medicament.

EXPERIMENTAL EXAMPLE 4

Absorption of a Medicament in Composition Coated with Polyurethane of the Present Invention in Oral Administration

Method

Compositions prepared in Example 14(d) and 15(d) were administered orally with 50 ml of water in beagle dogs fasting overnight. After given periods of time, the concentration of a medicament in blood was measured by high performance liquid chromatography.

Result

Figure 5:
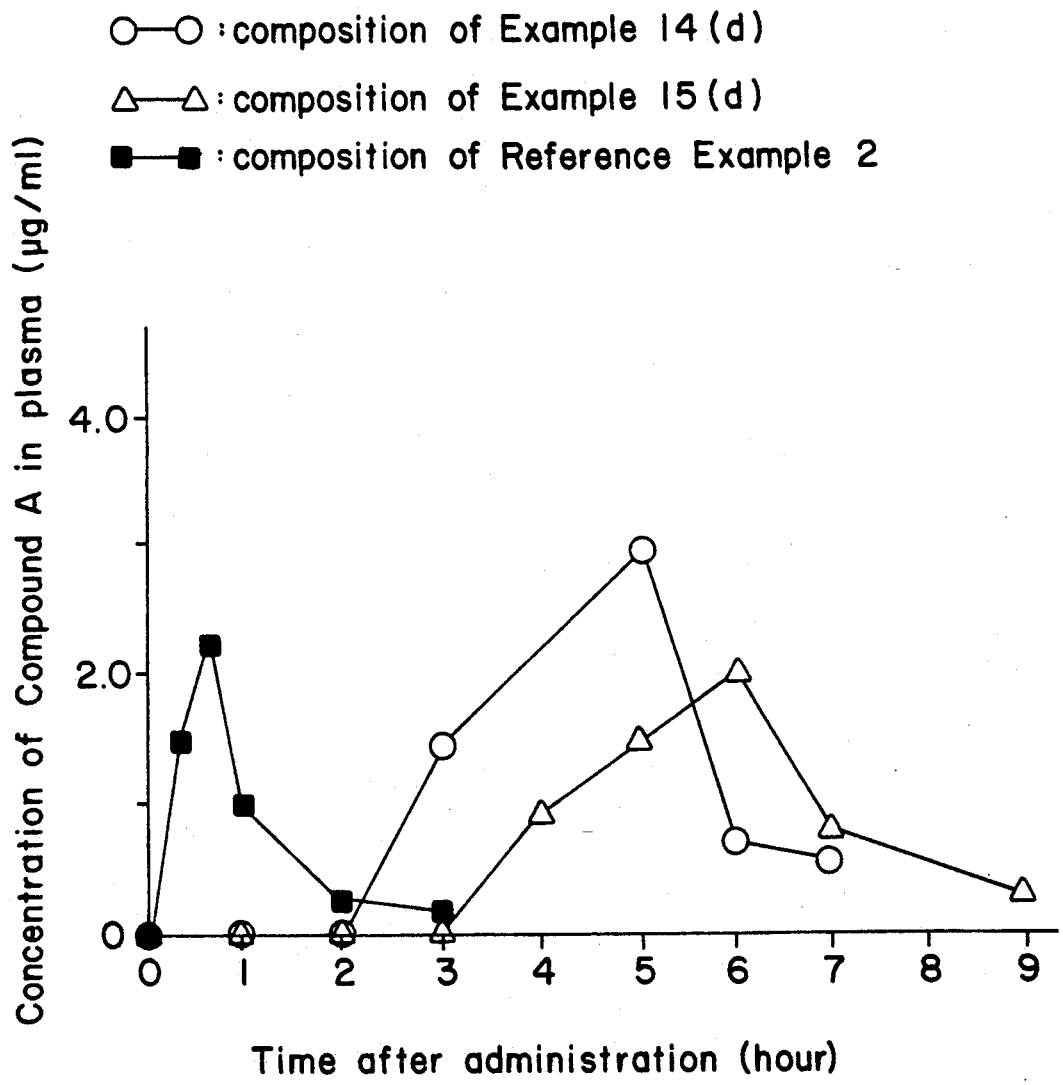
FIG. 5 is a graph showing the time-course of the concentration in blood, of a medicament in a composition coated with a polyurethane of the present invention, prepared in Example 14 (d) and 15 (d), and in a composition prepared in Reference Example 2, in oral administration.

The result is shown in FIG. 5.

Consideration

Considering the results of Experimental Example 3 that it takes a medicament about 3 hours to reach the ascending colon from the mouth, the result of the present experiment (that is, a medicament being released in blood 2 to 3 hours after administration) is reasonable. From the result, it is considered that the composition coated with polyurethanes of the present invention is an ideal composition which is not disintegrated before it reaches the colon, and is first degraded in the colon by the action of intestinal bacteria to release medicament.

What we claim is:

1. A polyurethane (1) of 1000 to 100,000 in average molecular weight, comprising plural segments, which are each structural units of A-B, A-C and A-D of the formula:

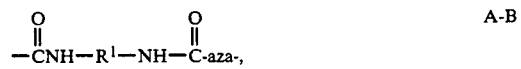
A-B

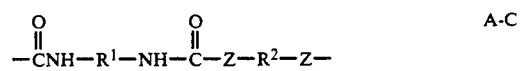
A-C and

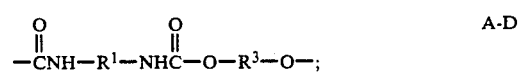
A-D the proportion of said segments A-B, A-C and A-D, is in the molar ratio 0.01 to 0.8:0 to 0.80:0 to 0.99, provided that the sum of the ratios A-B, A-C and A-D is 1.0;

each segment being produced by combining with repeat units of A,B,C and D of the formula:

A

B

C

D wherein
$R^1$ is a skeleton of a disocyanate and the three $R^1$'s in each of the segments A-B, A-C and A-D can be the same or different;
aza is a group of the formula:

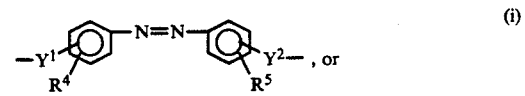
(i)

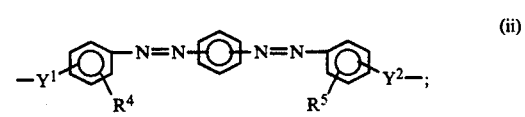
(ii)

wherein $Y^1$ and $Y^2$ which can be the same or different, are oxygen, imino (—NH—) or a group of the formula:

*R$^6$—O, *R$^6$—NH, O—R$^6$—O, *NHCO—R$^6$—NH or *CONH—R$_6$—NH;

wherein

R$^6$ C$_1$–C$_4$ is alkylene and an atom or the end of the group, marked by * is bonded to phenyl ring;

R$^4$ and R$^5$ each are, independently, hydrogen, halogen, nitro or phenyl;

R$^2$ is polyoxyalkylene glycol or diamine residue;

Z is oxygen or imino and the two Z's are the same;

R$^3$ is C$_1$–C$_6$ alkylene or a group of the formula:

R$^7$—O—R$^8$, R$^7$—NH—R$^8$ or R$^7$—N—R$^8$;
$\quad\quad\quad\quad\quad\quad\quad\quad\quad\quad\quad\quad$ |
$\quad\quad\quad\quad\quad\quad\quad\quad\quad\quad\quad\quad$ R$^9$ wherein R$^7$ and R$^8$, which can be the same or different, are C$_1$–C$_6$ alkylene; and R$^9$ is alkyl; each segment of the polyurethane being contained in the aforementioned proportion, is combined by block-type, random-type or a combination thereof.

2. A polyurethane according to claim 1, wherein R$^1$ is C$_4$–C$_8$ alkylene, or a divalent group of a benzene or cyclohexyl, both of which may be unsubstituted or substituted by one to four methyl groups, and may be linked to the cyanate residues either directly or via one of the methyl groups.

3. A polyurethane according to claim 1, wherein R$^1$ is selected from the group consisting of (CH$_2$)$_4$, (CH$_2$)$_6$, CH$_2$C(CH$_3$)$_2$CH$_2$CH$_2$CH(CH$_3$)CH$_2$, (CH$_2$)$_8$,

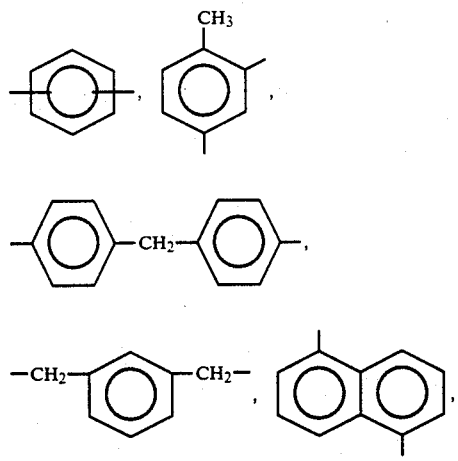

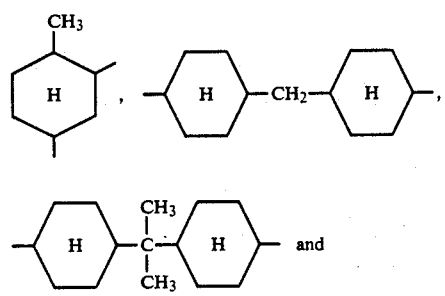

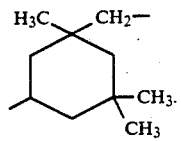

4. A polyurethane according to claim 1, wherein R$^1$ is selected from the group consisting of hexamethylene, xylylene and 3,5,5-trimethylcyclohexan-1-yl-3-ylmethyl.

5. A polyurethane according to claim 1, wherein aza is a group of the formula:

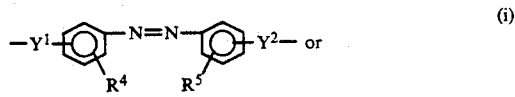

(i)

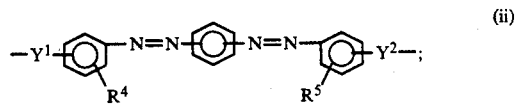

(ii)

wherein Y$^1$ and Y$^2$ which can be the same or different, are oxygen, imino or a group of the formula: *R$^6$—O or *R$^6$—NH (in which R$^6$ is C$_1$–C$_4$ alkylene) and R$^4$ and R$^5$ are hydrogen.

6. A polyurethane according to claim 1, wherein R$^2$ is a polymer residue of C$_1$–C$_4$ oxyalkylene glycol or diamine.

7. A polyurethane according to claim 1, wherein R$_3$ is C$_1$–C$_6$ alkylene or a group of the formula: R$^7$—O—R$^8$ in which R$^7$ and R$^8$ can be the same or different, are C$_1$–C$_6$ alkylene.

8. A polyurethane according to claim 1, wherein the proportion of segments, A-B:A-C is in the molar ratio less than 0.6:more than 0.4:A-B:A-D is in the molar ratio less than 0.2:more than 0.8; and A-B:A-C:A-D is in the molar ratio less than 0.2:less than 0.1:more than 0.7.

9. A polyurethane according to claim 1, wherein R$^1$ is a group of the formula:

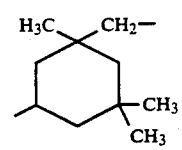

and the three R$^1$'s in each of segments A-B, A-C and A-D are the same, aza is a group of the formula:

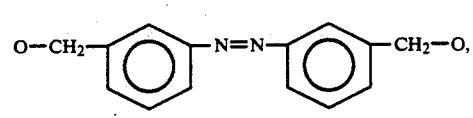

R$^2$ is polyoxyethylene glycol residue and R$^3$ is 1,2-propylene.

10. A pharmaceutical adjuvant containing a polyurethane as claimed in claim 1 as a main component.

* * * * *